(12) United States Patent
Levieux

(10) Patent No.: US 7,887,590 B2
(45) Date of Patent: Feb. 15, 2011

(54) INTERVERTEBRAL DISC PROSTHESIS

(75) Inventor: Jérôme Levieux, Geneva (CH)

(73) Assignee: Spineart SA, Geneva (CH)

( * ) Notice: Subject to any disclaimer, the term of this patent is extended or adjusted under 35 U.S.C. 154(b) by 0 days.

(21) Appl. No.: 11/913,336

(22) PCT Filed: May 2, 2006

(86) PCT No.: PCT/FR2006/000982

§ 371 (c)(1),
(2), (4) Date: Feb. 4, 2008

(87) PCT Pub. No.: WO2006/117474

PCT Pub. Date: Nov. 9, 2006

(65) Prior Publication Data

US 2008/0243253 A1    Oct. 2, 2008

(30) Foreign Application Priority Data

May 3, 2005    (FR) .................................. 05 04510

(51) Int. Cl.
*A61F 2/44* (2006.01)
(52) U.S. Cl. .............. 623/17.14; 623/17.11; 623/17.15; 623/17.16
(58) Field of Classification Search .... 623/17.11–17.16
See application file for complete search history.

(56) References Cited

U.S. PATENT DOCUMENTS

| | | | | |
|---|---|---|---|---|
| 4,759,766 A | * | 7/1988 | Buettner-Janz et al. | 623/17.15 |
| 5,370,697 A | * | 12/1994 | Baumgartner | 623/17.15 |
| 6,368,350 B1 | * | 4/2002 | Erickson et al. | 623/17.14 |
| 6,517,580 B1 | * | 2/2003 | Ramadan et al. | 623/17.15 |
| 6,849,224 B2 | * | 2/2005 | Wang et al. | 264/478 |
| 2004/0002761 A1 | * | 1/2004 | Rogers et al. | 623/17.13 |
| 2004/0143332 A1 | * | 7/2004 | Krueger et al. | 623/17.14 |
| 2004/0225363 A1 | * | 11/2004 | Richelsoph | 623/17.13 |
| 2005/0080488 A1 | * | 4/2005 | Schultz | 623/17.13 |
| 2006/0020341 A1 | * | 1/2006 | Schneid et al. | 623/17.14 |

FOREIGN PATENT DOCUMENTS

DE    203 15 611 U1    1/2004
DE    20 2004 009 542 U1    9/2004

OTHER PUBLICATIONS

French Preliminary Search Report FR 0504510 dated Dec. 20, 2005.
International Search Report PCT/FR2006/000982 dated Sep. 14, 2006.

* cited by examiner

*Primary Examiner*—Thomas C Barrett
*Assistant Examiner*—Michael T Schaper
(74) *Attorney, Agent, or Firm*—Miller, Matthias & Hull, LLP

(57) ABSTRACT

The invention relates to an intervertebral disc prosthesis having an upper plate, a lower plate having an essentially-flat support surface, and an intermediate element having a base which is equipped with a rim and which is topped with a spherical cap. The upper plate and the cap define a ball and socket joint therebetween. The base of the intermediate element comes into contact with a support surface of the lower plate. The lower plate is equipped with a guide having two edges which maintain the intermediate element therebetween. The rim of the base comes into contact with the edges, the rim being circular in shape and adapted to enable the intermediate element to roll along the length of the edges.

5 Claims, 1 Drawing Sheet

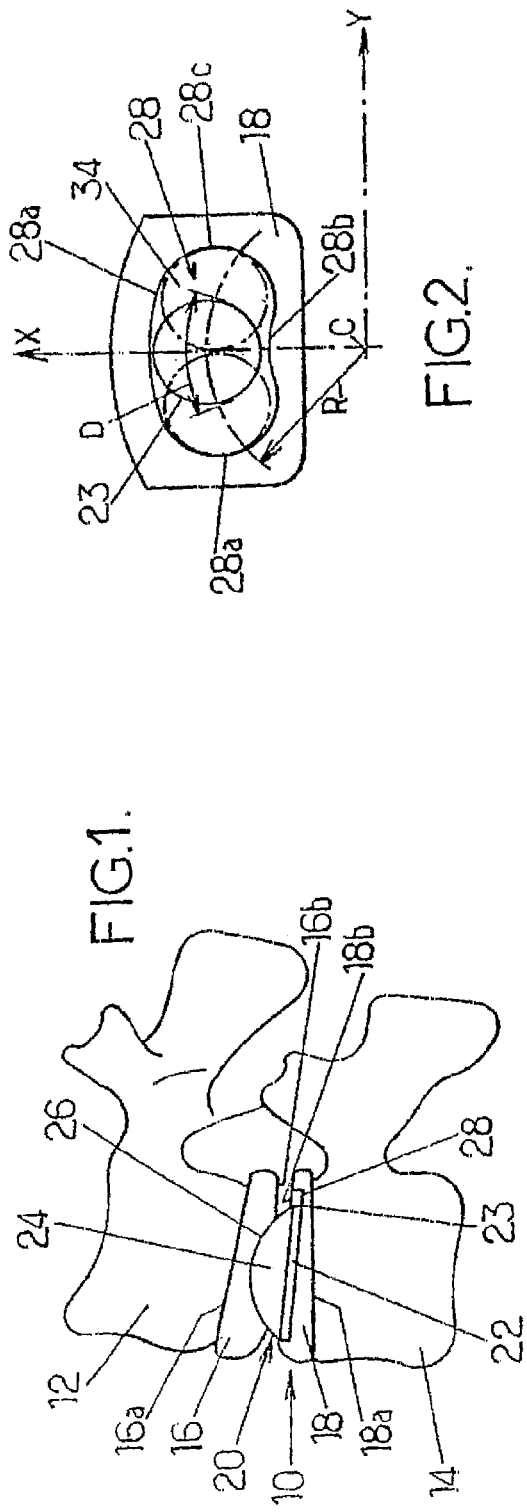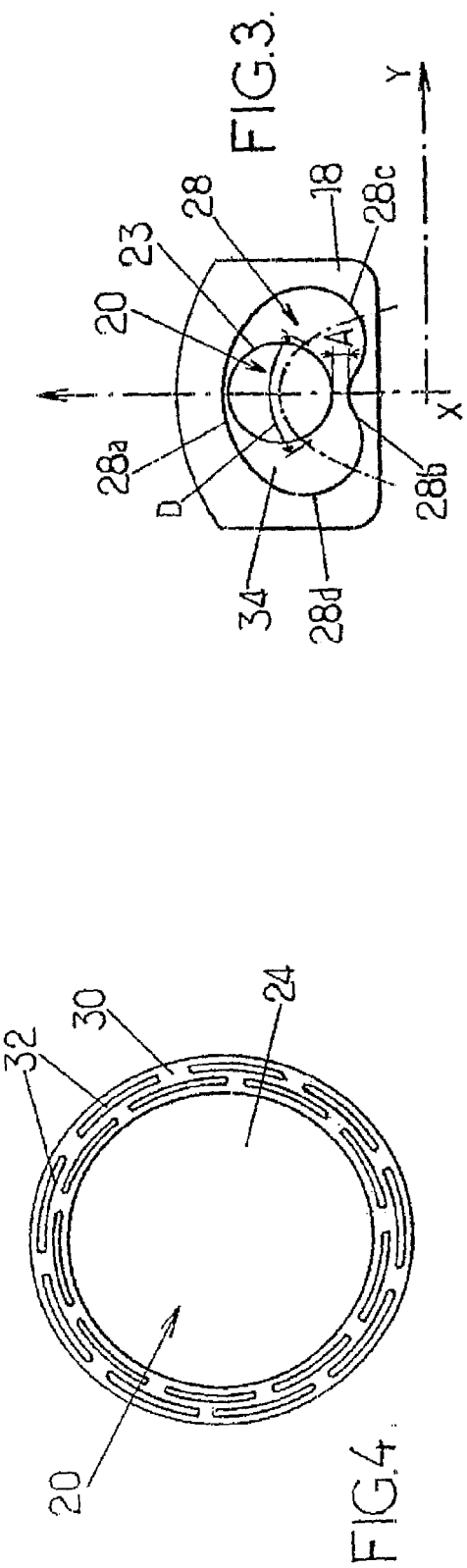

INTERVERTEBRAL DISC PROSTHESIS

FIELD OF THE DISCLOSURE

The present invention relates to intervertebral disc prostheses.

More particularly, the invention relates to an intervertebral disc prosthesis comprising an upper plate, a lower plate having an essentially flat support surface and an intermediate element comprising a base having a rim and surmounted by a spherical cap, i.e. a volume forming a projection, the upper plate having an indentation complementary to the spherical cap and coming into contact with said cap so as to define a ball and socket joint between the upper plate and the intermediate element, the base of the intermediate element coming into contact with the support surface, the lower plate having a guide comprising two front and rear edges facing each other, maintaining between them an essentially constant distance and holding between them the intermediate element, the rim of the base coming into contact with at least one of the edges.

BACKGROUND OF THE DISCLOSURE

US 2004/0143332-A1 describes a prosthesis of the type described previously in which the intermediate element is moved along an arc-of-circle trajectory by sliding in a rail.

However the different elements constituting the prosthesis can be subjected to localized friction which can damage the optimal operation of the prosthesis in the long term.

DE 203 15 611 U relates to an intervertebral disc prosthesis, the cap of which is maintained centrally with respect to a recess and surrounded by shock absorbers. Only a so-called "anteroposterior" movement from front to rear is possible, without the possibility of movement by rolling of the intermediate element along the edges. The edges with which the intermediate element is in contact are the lateral edges of the prosthesis.

US-A-04/0002761 describes an intervertebral disc prosthesis comprising a concave element. Only an anteroposterior movement is possible and in particular not a movement by rolling of the intermediate element along the anterior and posterior edges of the prosthesis.

SUMMARY OF THE DISCLOSURE

The purpose of the present invention is in particular to propose a prosthesis having an improved service life compared with the prostheses of the prior art.

To this end, according to the invention, a disc prosthesis of the kind in question is characterized in that the rim is circular in form and is suited to allow the movement by rolling of the intermediate element along the edges.

By means of these arrangements, the prosthesis no longer has any localized points of wear, by replacing the contact by friction on the edges of the guide by rolling, which makes it possible to increase the duration of optimal use of the prosthesis.

In various embodiments of the prosthesis according to the invention, it is optionally possible also to use one and/or other of the following arrangements:

- the edges of the guide have a non-circular conic type shape, so as to guide the intermediate element along a conic-type trajectory;
- the edges of the guide are parabolic in shape;
- the intermediate element can be displaced, for each point on the trajectory, along an axis perpendicular to a tangent at a point of the trajectory, by a value comprised between 0.1 and 3 mm between the two edges of the guide;
- the amplitude of movement of the intermediate element along the trajectory is 0.01 to 2 times the diameter of the base 22;
- the guide is a recess made in the lower plate;
- the base of the intermediate element has an outer peripheral circular flange comprising several slots, so as to absorb the shocks between the edges of the guide and the flange by deformation of said flange;
- the flange is made of high molecular weight polyethylene material.

Other characteristics and advantages of the invention will become apparent on reading the following description of one of its embodiments, given as a non-limitative example, with reference to the attached drawings.

BRIEF DESCRIPTION OF THE DRAWINGS

In the drawings:

FIG. 1 represents a vertical cross-sectional view of the prosthesis according to the invention arranged between two vertebrae;

FIG. 2 represents an elevational view of part of a prosthesis according to a first embodiment variant;

FIG. 3 represents an elevational view of part of the prosthesis according to a second embodiment variant;

FIG. 4 represents an elevational view of the intermediate element according to a third embodiment variant.

In the different figures, the same references denote identical or similar elements.

DETAILED DESCRIPTION

The present invention relates to a disc prosthesis 10 which is intended to be arranged between two vertebrae of a vertebral column 12, 14. For example FIG. 1 illustrates a side view of two vertebrae 12, 14 of a vertebral column between which the prosthesis 10 according to the invention is arranged. This type of prosthesis 10 can be used to replace an intervertebral disc subject to degeneration resulting from trauma, diseases or age.

These kinds of degeneration can result in an alteration of the natural space between two vertebrae. The narrowing of this natural space can result in a pressure which is exerted on certain nerves, and consequently pain can occur.

The disc prosthesis according to the invention can therefore be used to maintain the natural space between two vertebrae.

It must also allow the vertebrae to be moved in relation to each other according to a natural movement. In particular, it must allow a movement of axial rotation which corresponds in part to the movement of rotation of the trunk or neck in the cervical region of the human body, an anteroposterior movement which corresponds to a movement of flexion or extension of the upper part of the body or the head in the cervical region, and a lateral movement which corresponds to an inclination of the upper part of the body, or the neck in the cervical region.

The disc prosthesis 10 according to the invention comprises an upper plate 16 and a lower plate 18 each having an external face 16a, 18a oriented towards an upper vertebra and a lower vertebra respectively. On each of the external faces 16a, 18a, teeth are arranged, not shown, which allow the anchoring of the plates 16, 18 in the vertebrae.

The upper 16 and lower plates 18 also each comprise an internal surface 16b, 18b. The internal surfaces extend laterally along a first anteroposterior axis X and extend longitudinally along a second axis Y perpendicular to the first axis, facing each other and they are in contact with an intermediate element 20.

The intermediate element 20 has a circular base 22 having a circular rim 23. The base 22 is surmounted by an upper spherical cap 24. The base 22 is mounted in a mobile fashion on the internal surface 18b of the lower plate 18, and the spherical cap 24 cooperates with an indentation 26 produced in the internal surface 16b of the upper plate 16. This indentation 26 has a spherical profile, which makes it possible to obtain a ball and socket joint between the spherical cap 24 of the intermediate element 20 and the upper plate 16.

The upper plate 16 is made of a material of the chromium-cobalt or titanium or stainless steel type and the intermediate element is made of a plastic material, of high density polyethylene type, having very good sliding characteristics.

The ball and socket joint between the upper plate 16 fixed to the upper vertebra 12 and the intermediate element 20 itself connected to the lower vertebra 14 by the lower plate 18 makes it possible to reproduce the movements of flexion or extension and the movements of inclination between two vertebrae 12, 14 of a vertebral column.

FIG. 3 represents an elevational view of the internal surface 18b of the lower plate 18 and of the intermediate element 20. The internal face 18b of the lower plate 18 has a recess 28 which guides the movement of the intermediate element 20. As represented in FIG. 3, the recess 28 is "kidney"-shaped, delimited by an essentially flat support surface 34, a front edge 28a, a rear edge 28b and two extreme edges 28c, 28d, connecting the front edge 28a and the rear edge 28b. The front edge 28a and the rear edge 28b are symmetrical with respect to the anteroposterior axis (X) and each essentially have a conic type shape, illustrated in FIG. 3 by a parabolic shape open towards the rear along the anteroposterior axis.

It is also possible for the edges (28a, 28b, 28c, 28d) to form a succession of conics.

In FIG. 3, the anteroposterior axis X represented is the axis of symmetry of the parabolic trajectory. The parabolic trajectory is represented by the broken line which corresponds to the median line between the two edges 28a, 28b.

This feature allows the intermediate element 20 to be moved according to a trajectory of conic type such as an arc of a circle, a portion of a parabola, a hyperbola or an ellipse, or of conic-succession type, such as several adjacent arcs of circles, which confers upon the intermediate element a movement closer to the real movement of rotation between two vertebrae.

In FIG. 2, the trajectory represented is an arc of a circle.

In FIG. 3, the trajectory represented is a parabola, the reduced Cartesian equation of which is of the type $$y^2 = 2px.$$

Moreover, the amplitude of movement D along the conic-type trajectory, between two extreme edges, is of the order of 0.01 to 2 times the diameter of the base 22 of the intermediate element 20, so as to respond to different pathological cases and allow the patient to recover the ability to achieve a movement close to the real movement.

Moreover, the recess 28 is made such that the intermediate element 20 can translate from front to rear in order to obtain a translation towards the rear of the intermediate element during a movement of flexion, and a translation towards the front of the intermediate element 20 during a movement of extension.

The amplitude A of these movements from the front towards the rear, along the trajectory, is advantageously comprised, depending on the pathological cases, between 0.1 and 3 mm, and preferably between 0.5 and 3 mm, for each point of the trajectory, along an axis perpendicular to a tangent at the point of the trajectory.

This feature of the recess 28 makes it possible to obtain a prosthesis capable of reproducing a natural intervertebral joint in particular during a combined movement of flexion and rotation.

When the base 22 of the intermediate element 20 is moved in the recess 28 produced on the internal surface 18b of the lower plate 18, the rim 23 of the base 22 comes into contact with the edges 28a, 28b of the recess 28. The movement of the intermediate element 20 is then obtained by rolling of the intermediate element 20 along the edges 28a, 28b delimiting the recess 28, which avoids premature wear phenomena due to friction as during a contact by pure sliding. Sliding between the bottom of the base 22 and the support surface of the recess 28 can be obtained if the support surface of the recess 28 is treated in order to improve its sliding characteristics (for example a polymirror treatment, or nitride coating) and if the bottom of the base is made of high molecular weight polyethylene, in order to limit the friction during the movement of the intermediate element 20 and consequently premature wear.

For example if the edges of the recess have the shape of an arc of a circle, each point of the rim 23 of the base 22 will describe a cycloidal curve.

According to a variant of the invention represented in FIG. 4, the base of the intermediate element comprises an outer peripheral circular flange 30 which comprises several slots 32 passing through or not passing through, so as to absorb the shocks between the edges 28a, 28b of the recess 28 and the flange 30. In fact, the flange 30 is made of a material of high molecular weight polyethylene type or any other bio-compatible material having good shock-absorbing characteristics, which with the presence of the slots 32 has a deformation capacity sufficient to absorb the contact when the intermediate element comes to a stop against the edges 28a, 28b of the recess 28. This makes it possible to limit the joint pain experienced by the patient.

The invention claimed is:

1. An intervertebral disc prosthesis comprising:
   an upper plate,
   a lower plate having a substantially flat support surface,
   an intermediate element comprising a base having a rim and surmounted by a spherical cap,
   the upper plate having an indentation having exactly the same radius of curvature as the spherical cap and coming into contact with said cap so as to define a ball and socket joint between the upper plate and the intermediate element,
   the base of the intermediate element coming into contact with the support surface,
   the lower plate having a guide which is a closed recess in the lower plate, said guide comprising an anterior edge and a posterior edge facing each other, maintaining between them a substantially constant distance and holding between them the intermediate element,
   the rim of the base coming into contact with at least one of the anterior edge and posterior edge, wherein the rim is a circle in cross-section and is suited to allow the movement by rolling of the intermediate element along the anterior edge and posterior edge;

wherein the edges of the guide have a non-circular conic type shape, so as to guide the intermediate element along a conic-type trajectory; wherein the edges of the guide have a parabolic shape.

2. The disc prosthesis according to claim 1, wherein the intermediate element can be displaced according to a trajectory, for each point on the trajectory, along an axis perpendicular to a tangent at the point of the trajectory, by a value comprised between 0.1 and 3 mm between the two edges.

3. The disc prosthesis according to claim 2, wherein the circular rim has a diameter and the amplitude of movement of the intermediate element along the trajectory is from 0.01 to 2 times the diameter of the base.

4. The disc prosthesis according to claim 1, wherein the rim of the base of the intermediate element has an outer peripheral circular flange comprising several slots, so as to absorb the shocks between the edges of the guide and the flange by deformation of said flange.

5. The disc prosthesis according to claim 4, wherein the flange is made of high-molecular-weight polythene material.

* * * * *